United States Patent
Gudaitis et al.

(10) Patent No.: US 7,034,942 B2
(45) Date of Patent: Apr. 25, 2006

(54) COLOR MEASUREMENT DEVICE AND COLOR MEASUREMENT METHOD

(75) Inventors: Algird M Gudaitis, Vancouver, WA (US); Sam M. Sarmast, Vancouver, WA (US); Tod S. Heiles, Vancouver, WA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 1000 days.

(21) Appl. No.: 10/041,858

(22) Filed: Jan. 7, 2002

(65) Prior Publication Data

US 2003/0128362 A1 Jul. 10, 2003

(51) Int. Cl.
*G01J 21/25* (2006.01)
(52) U.S. Cl. .................................. 356/419; 356/420
(58) Field of Classification Search ................ 356/416, 356/419, 420
See application file for complete search history.

(56) References Cited

U.S. PATENT DOCUMENTS 5,570,192 A * 10/1996 Terauchi et al. ............ 356/419
6,603,551 B1 * 8/2003 Mestha et al. .............. 356/416
6,791,676 B1 * 9/2004 Meller ........................ 356/416

OTHER PUBLICATIONS

HP Patent Application, U.S. Appl. No. 09/768,662, "Color Measurement With Distributed Sensors in A Color Hard Copy Apparatus", filed Jan. 23, 2001.
HP Patent Application, U.S. Appl. No. 09/970,419, "Compact Optical Sensing System", filed Oct. 2, 2001.
HP Patent Application, U.S. Appl. No. 09/970,278, "Color Calibration Color Value Correction", filed Oct. 2, 2001.
HP Patent Application, U.S. Appl. No. 09/969,745, "Tuning System For A Compact Optical Sensor", filed Oct. 2, 2001.
HP Patent Application, U.S. Appl. No. 09/970,196, "Calibrating System For A Compact Optical Sensor", filed Oct. 2, 2001.

* cited by examiner

*Primary Examiner*—Samuel A. Turner
*Assistant Examiner*—Kara Geisel
(74) *Attorney, Agent, or Firm*—Gregg W. Wisdom

(57) ABSTRACT

A method, includes illuminating a first portion of a colored region with first light from a gas discharge tube and generating a first output using a diffuse reflection of the first light from the first portion. The method further includes illuminating a second portion of the colored region with second light from a first solid state lamp and generating a second output using a diffuse reflection of the second light from the second portion. Additionally, the method includes illuminating a third portion of the colored region with third light from a second solid state lamp and generating a third output using a diffuse reflection of the third light from the third portion.

20 Claims, 11 Drawing Sheets

COLOR MEASUREMENT DEVICE AND COLOR MEASUREMENT METHOD

INTRODUCTION

Imaging devices, such as inkjet printers, inkjet facsimile machines, electrophotographic printers, electrophotographic facsimile machines, electrophotographic copiers, and the like, form images on media by placing colorant onto media. Electrophotographic imaging devices form images by transferring developed latent electrostatic images formed of a colorant, such as toner particles, onto media and fixing the toner to the media. The latent electrostatic images are typically formed by exposing a photoconductor to a pulsating laser beam that repeatedly sweeps across the photoconductor while the surface of the photoconductor moves perpendicular to the direction of movement of the laser beam. The laser beam is pulsed according to a single bit stream of digital data derived from the data defining the image that is to be formed.

Some electrophotographic imaging devices form color images by successively transferring a developed latent electrostatic image for each color plane (cyan, magenta, yellow, and black color planes) using a single set of hardware (photoconductor, charging device, laser scanner, developing device, etc.) Other electrophotographic imaging devices include separate sets of hardware for each color plane to form and develop the latent electrostatic image and transfer the developed latent electrostatic image to media.

Inkjet imaging devices form images by ejecting drops of a colorant, such as ink, onto the media using printheads for each of the ink colors. There is relative movement between the printheads and media while ejecting ink droplets from orifices included within the printheads. The printheads eject ink according to electrical signals derived from data defining the image that is to be formed. Typically the ink colors used to form color images include cyan, magenta, and yellow ink. By ejecting various combinations of quantities of the different color inks onto the media, a wide range of colors can be reproduced on the media. In addition, many inkjet printers make use of black ink for forming text characters and black regions of images.

The color of a region formed on a surface or displayed on a monitor can be characterized by color space values in any of a variety of color spaces. For example, colors values for the region could be characterized by values expressed in an RGB color space, a CMYK color space, an XYZ color space, an L*a*b* color space, or an L*u*v* color space. Accurately reproducing the color of the region on media using an imaging device involves careful control of the quantity and placement of the colorants used to form the image corresponding to the region. Typically, imaging devices capable of producing color images undergo color calibration so that after completion of the color calibration process the actual color formed in response to color data reproduces the intended color corresponding to the color data with the desired accuracy. The color calibration process may involve the formation of several regions of varying colors by the imaging device. Measurements of the colors of the regions provides data used to adjust the quantities of colorants that are applied in response to color data so that the intended color can be produced with the desired accuracy.

Accurate measurement of the colors of the regions formed during the color calibration process is useful for effectively performing the color calibration. A color measuring device, such as a spectrophotometer, that can accurately measure the spectrum of diffuse visible light reflected from the regions formed for color calibration could provide measurements of the color of sufficient accuracy for the calibration process. However, this kind of measuring device is very expensive. A lower cost measuring device of sufficient accuracy could be usefully applied in imaging devices for performing color calibrations.

SUMMARY OF THE INVENTION

A method includes illuminating a first portion of a colored region with first light from a gas discharge tube and generating a first output using a diffuse reflection of the first light from the first portion. The method further includes illuminating a second portion of the colored region with second light from a first solid state lamp and generating a second output using a diffuse reflection of the second light from the second portion. In addition, the method includes illuminating a third portion of the colored region with third light from a second solid state lamp and generating a third output using a diffuse reflection of the third light from the third portion.

DESCRIPTION OF THE DRAWINGS

A more thorough understanding of embodiments of the color measurement device may be had from the consideration of the following detailed description taken in conjunction with the accompanying drawings in which:

Shown in FIG. 1 is an embodiment of an inkjet printer.

Figure 2:
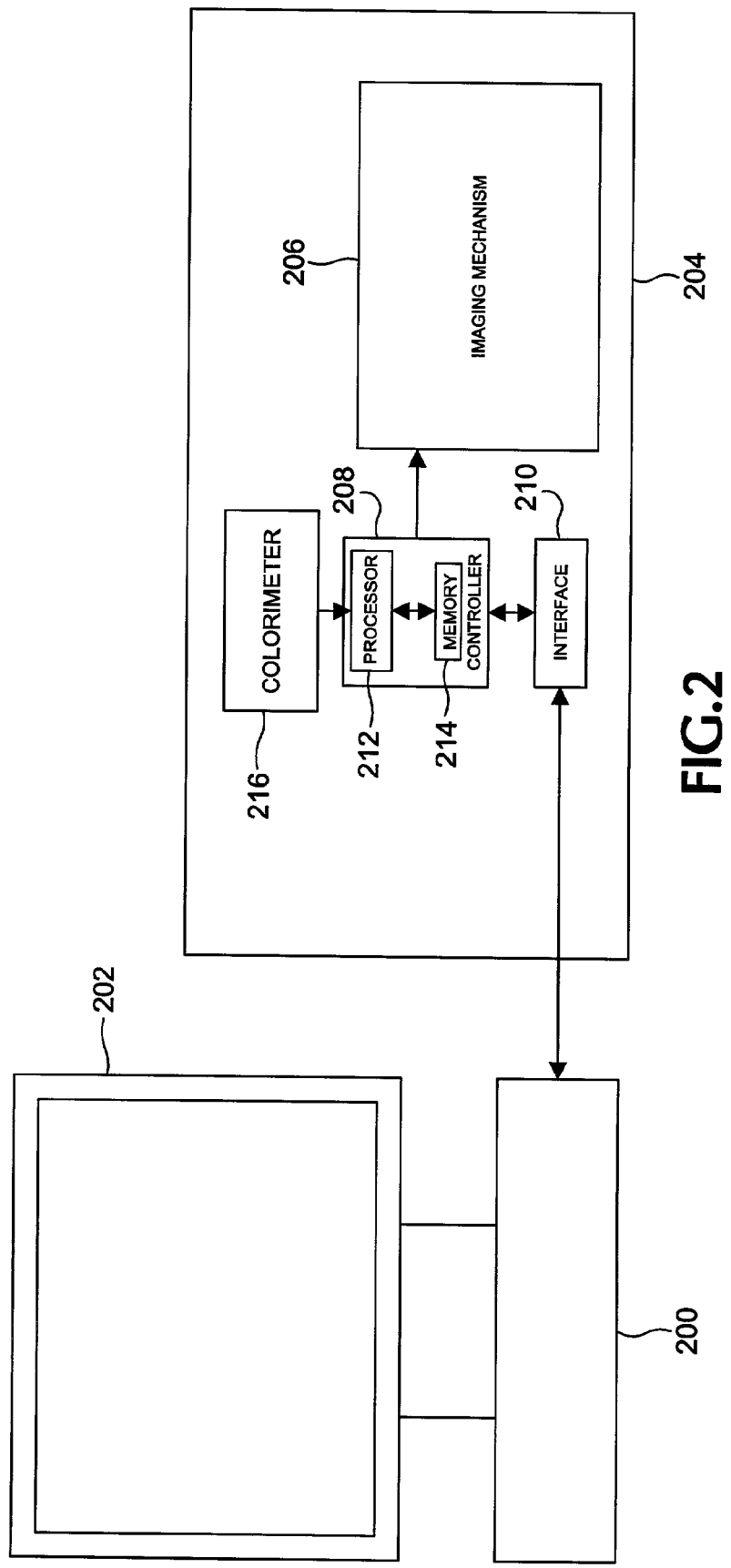

Shown in FIG. 2 is a high level block diagram of an embodiment of an imaging device including an embodiment of the color measurement device.

Figure 3:
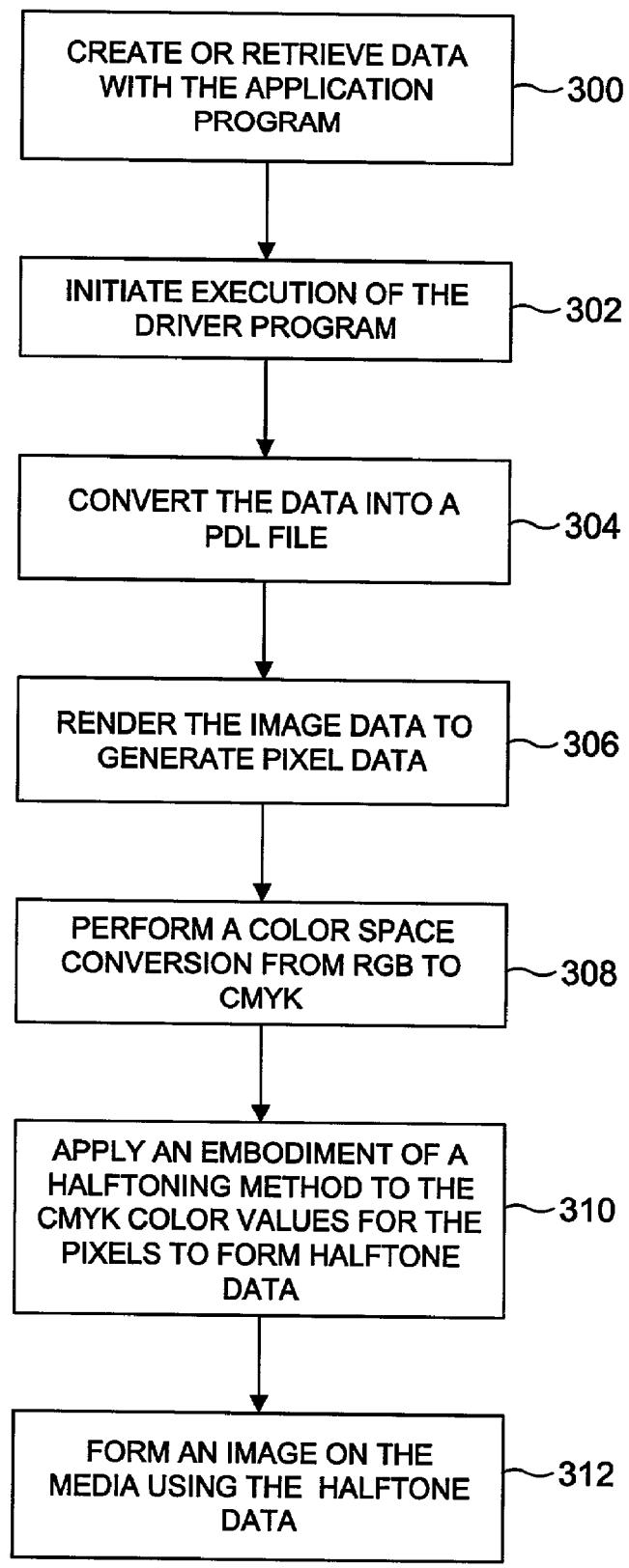

Shown in FIG. 3 is a high level flow diagram of a method for using the embodiment of the imaging device to form an image on media.

Figure 4:
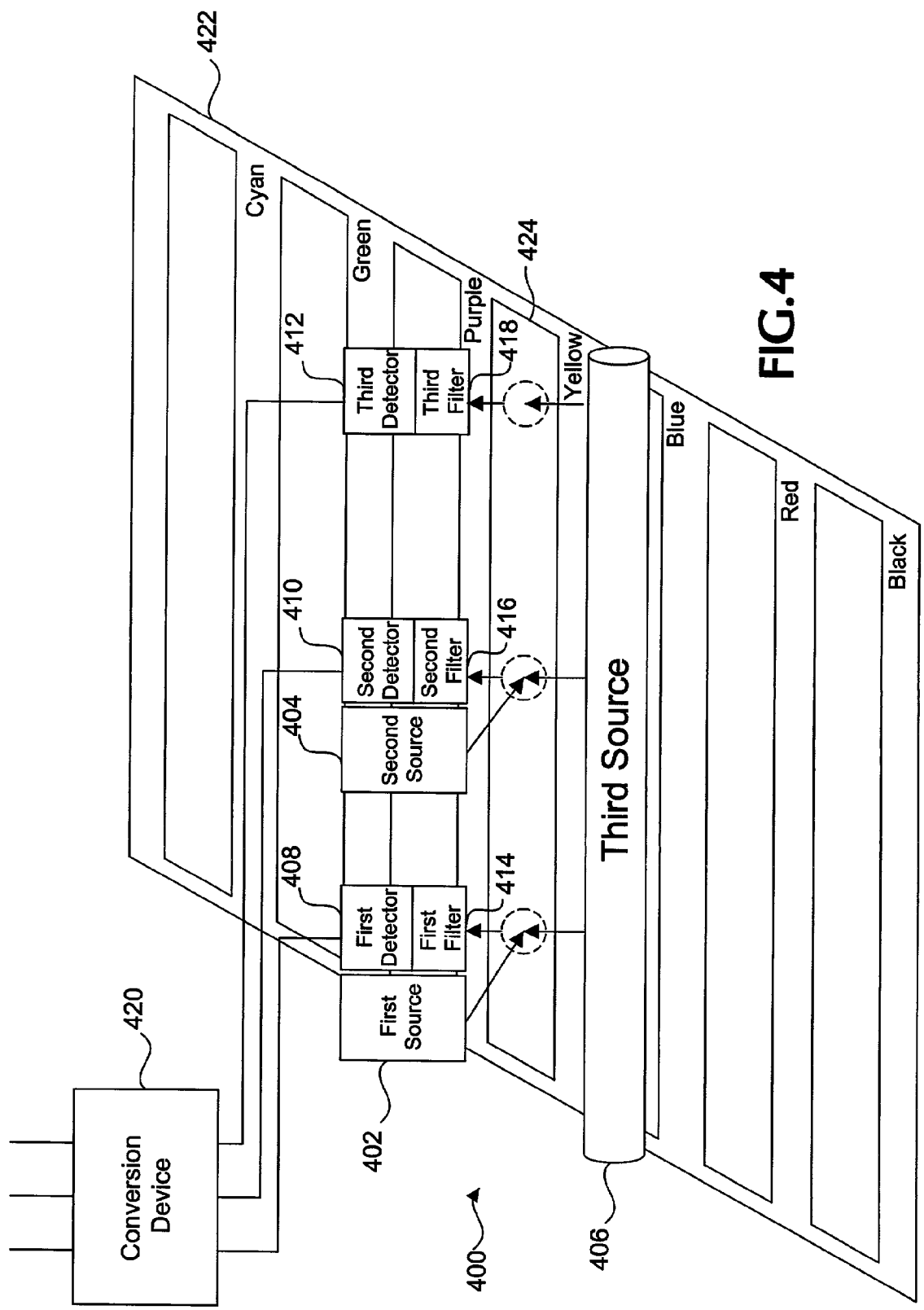

Shown in FIG. 4 is a high level block diagram of a first embodiment of the color measurement device.

Figure 5:
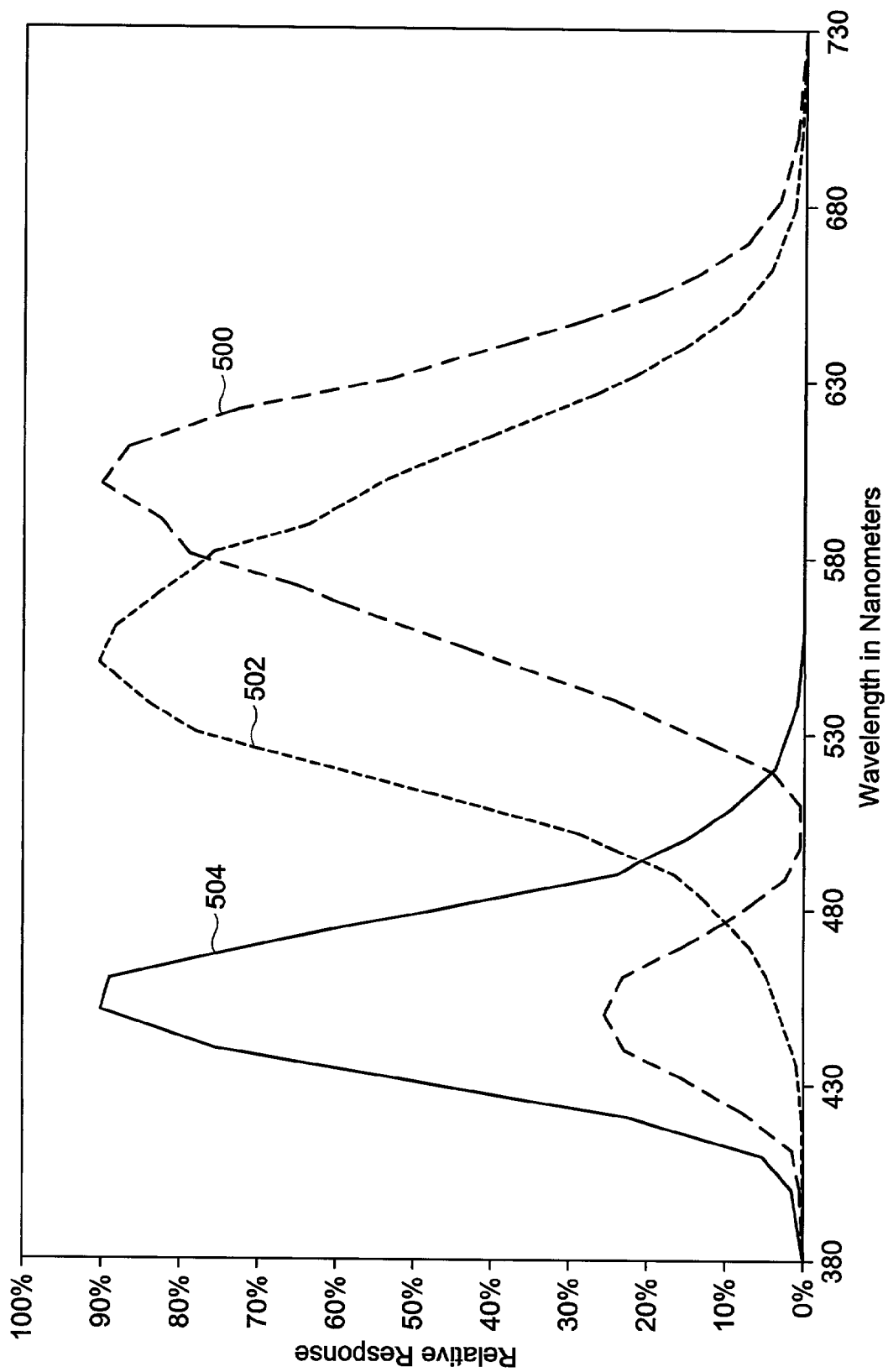

Shown in FIG. 5 are color matching functions for the XYZ tristimulus color space.

Figure 6A:
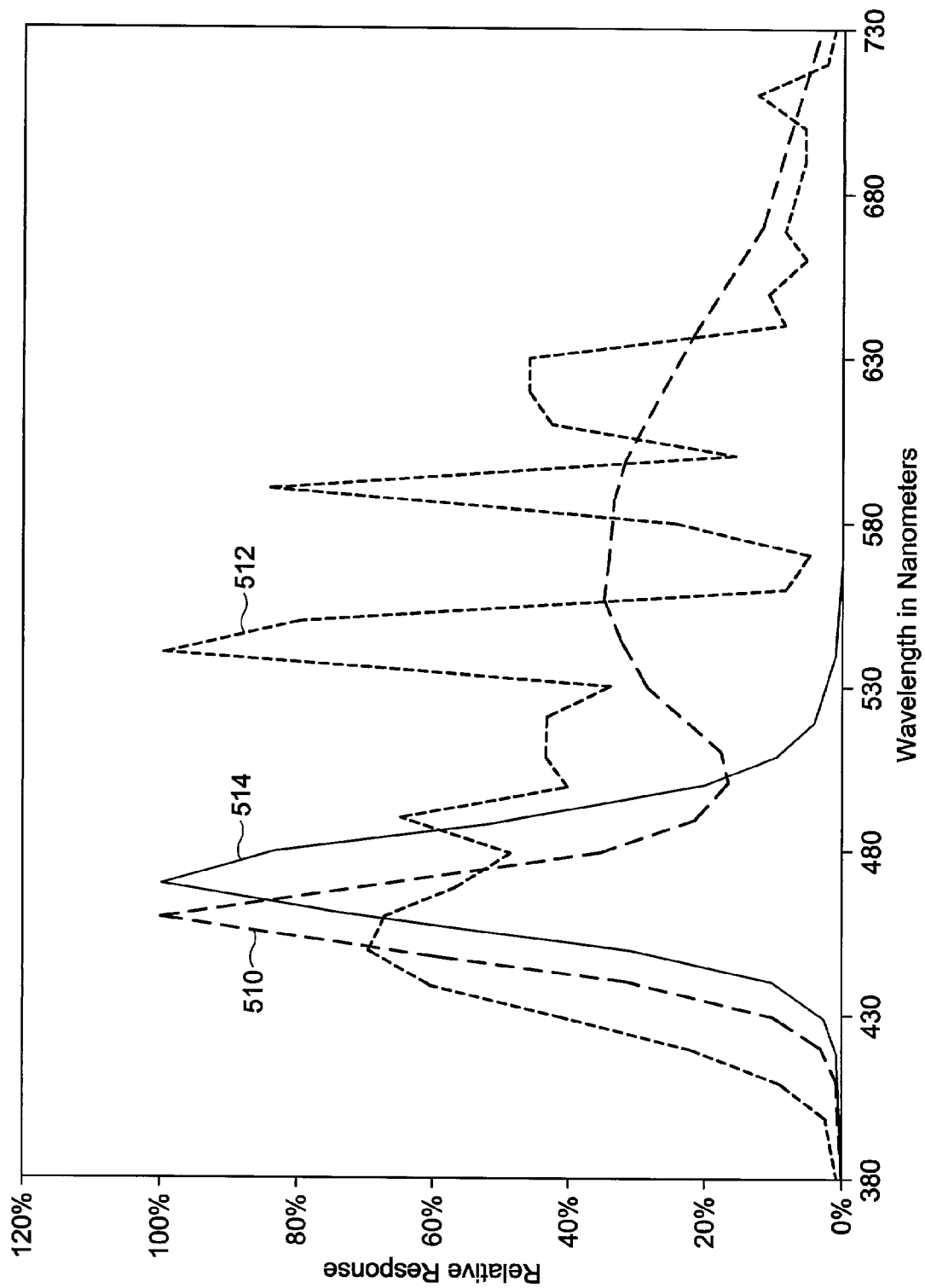

Shown in FIG. 6A are representative spectral emission curves for sources used in embodiments of the color measurement device.

Figure 6B:
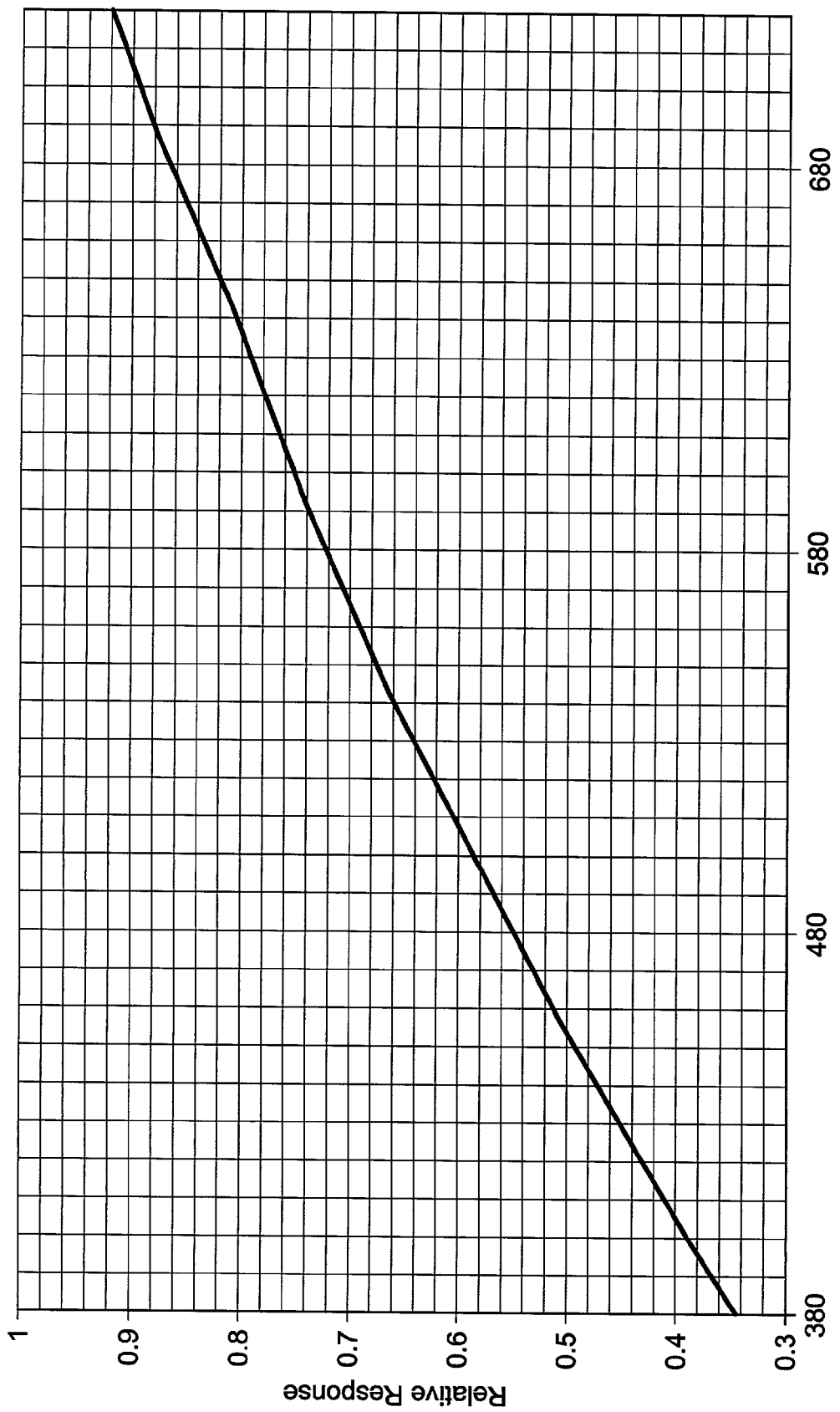

Shown in FIG. 6B is a representative spectral response curve for a detector.

Figure 7:
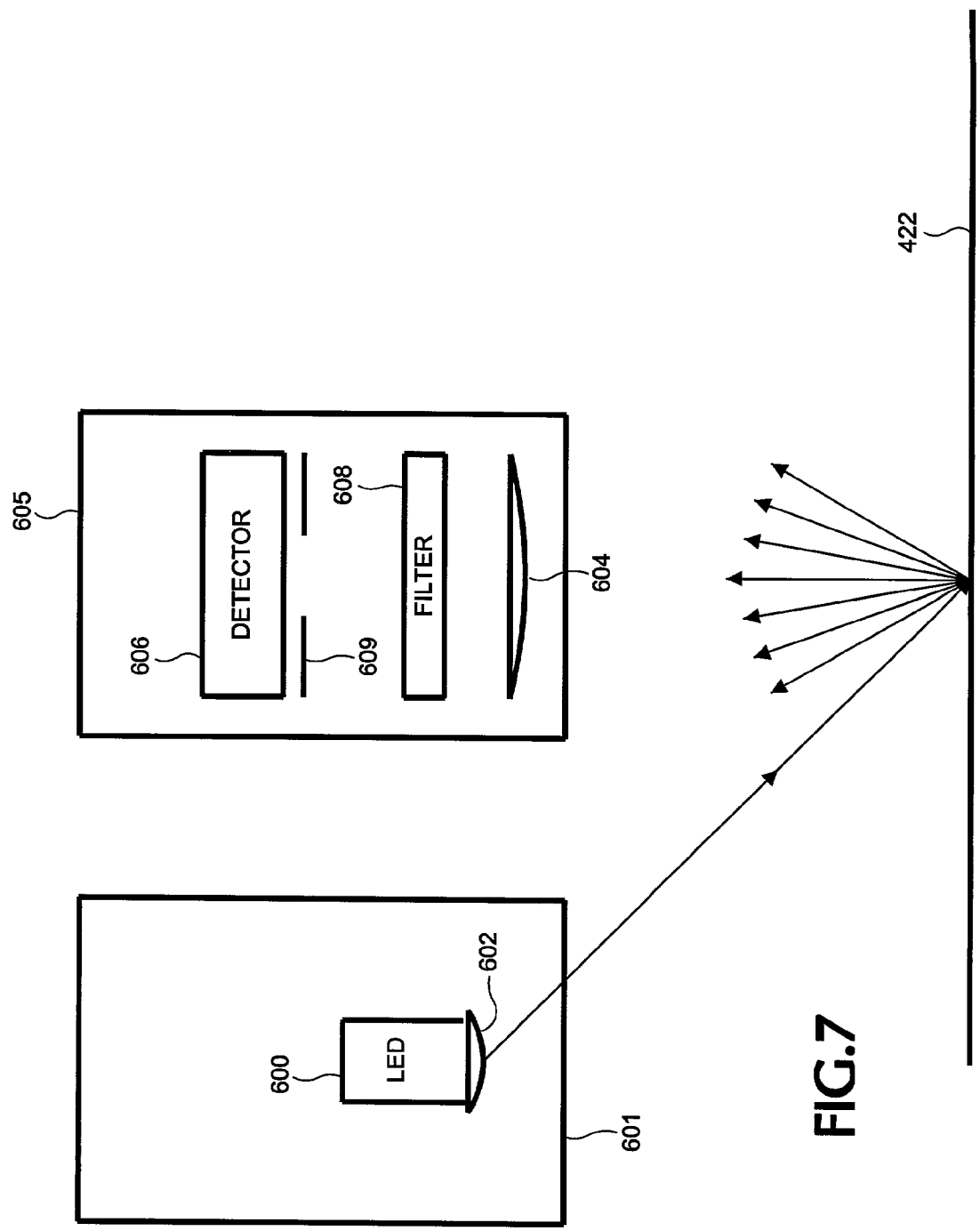

Shown in FIG. 7 is a representation of a light source, filter, and detector arrangement that could be used in embodiments of the color measurement device.

Figure 8:
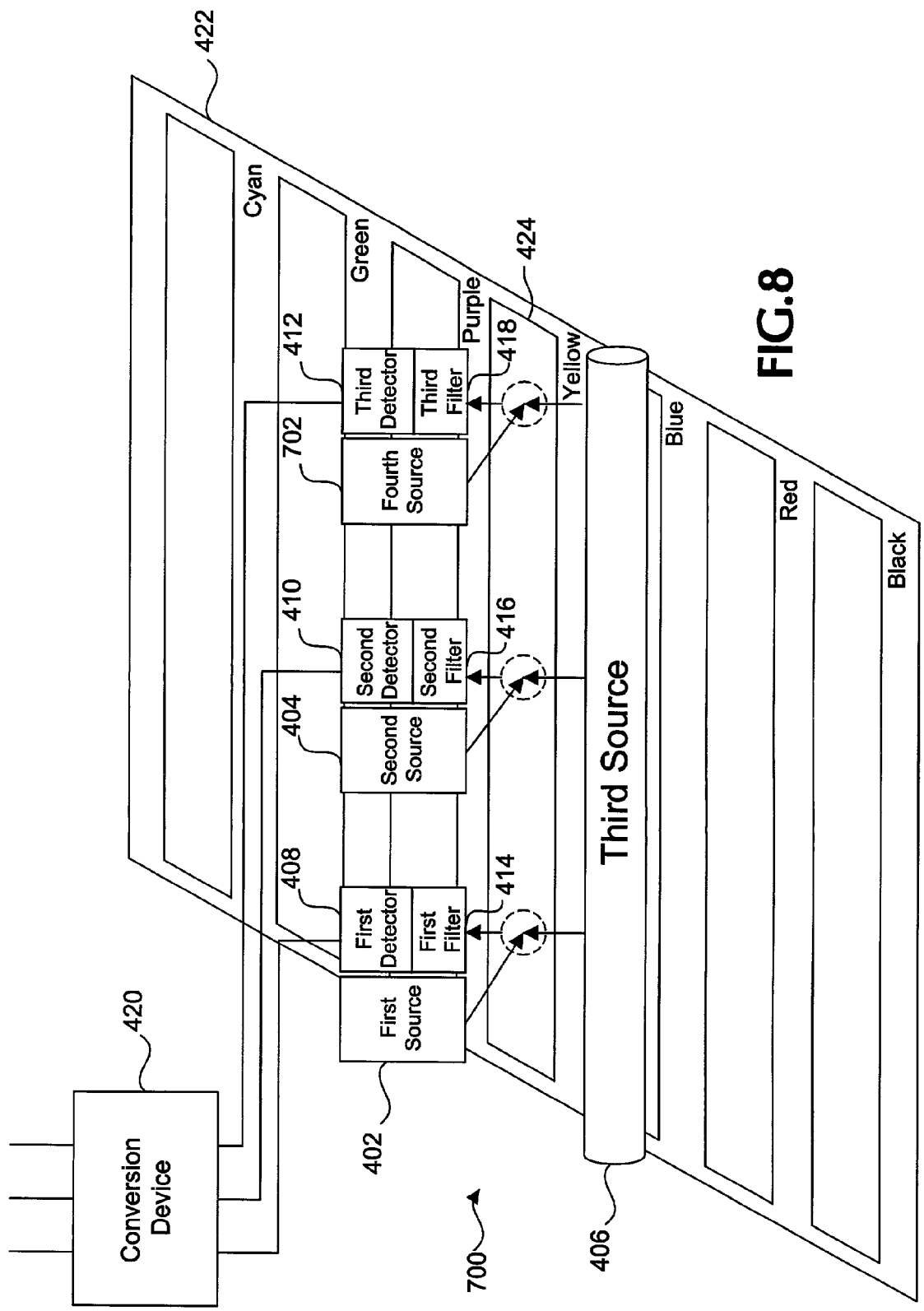

Shown in FIG. 8 is a simplified block diagram showing an arrangement of sources and detectors in a second embodiment of the color measurement device.

Figure 9:
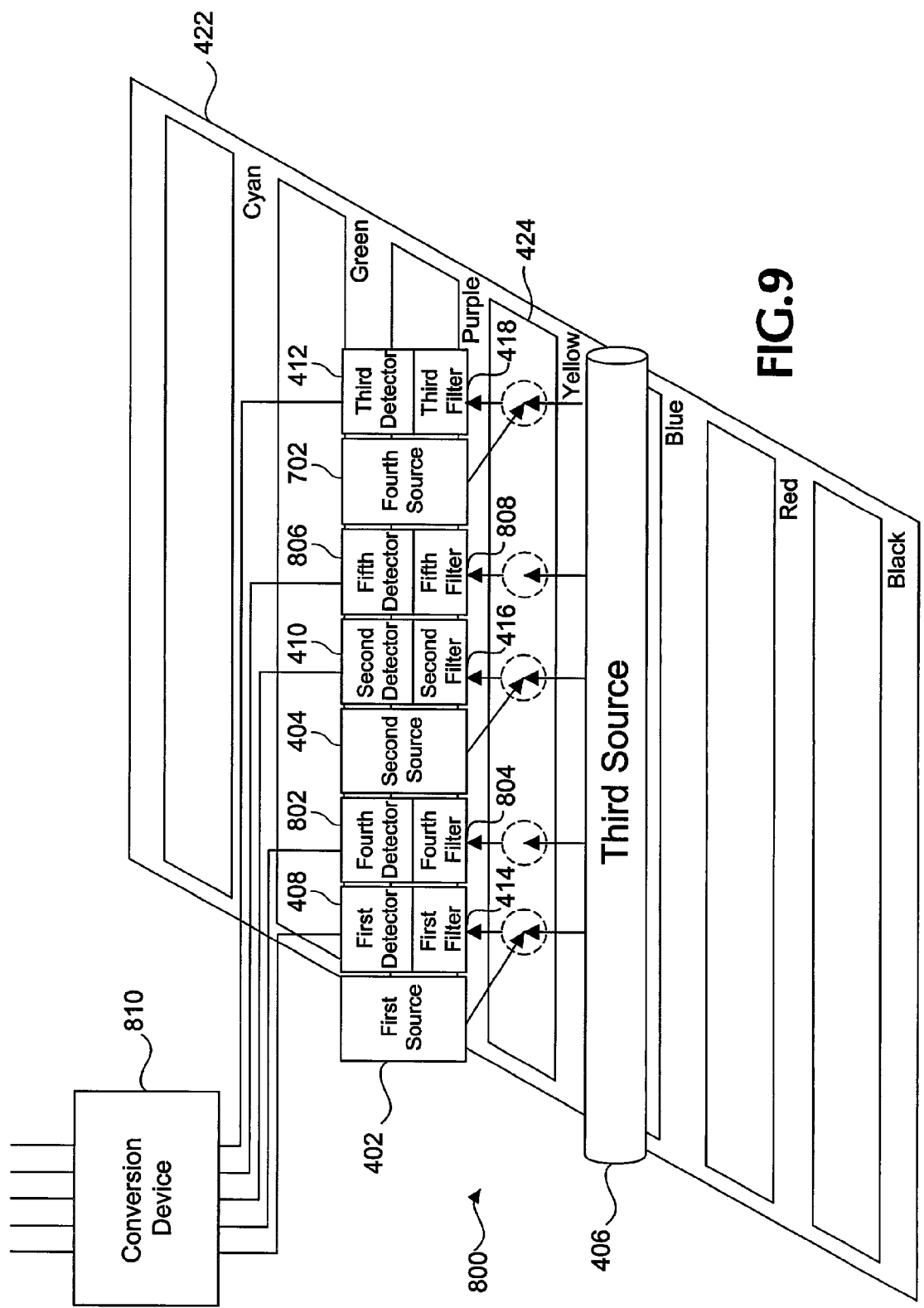

Shown in FIG. 9 is a simplified block diagram showing an arrangement of sources and detectors in a third embodiment of the color measurement device.

Figure 10:
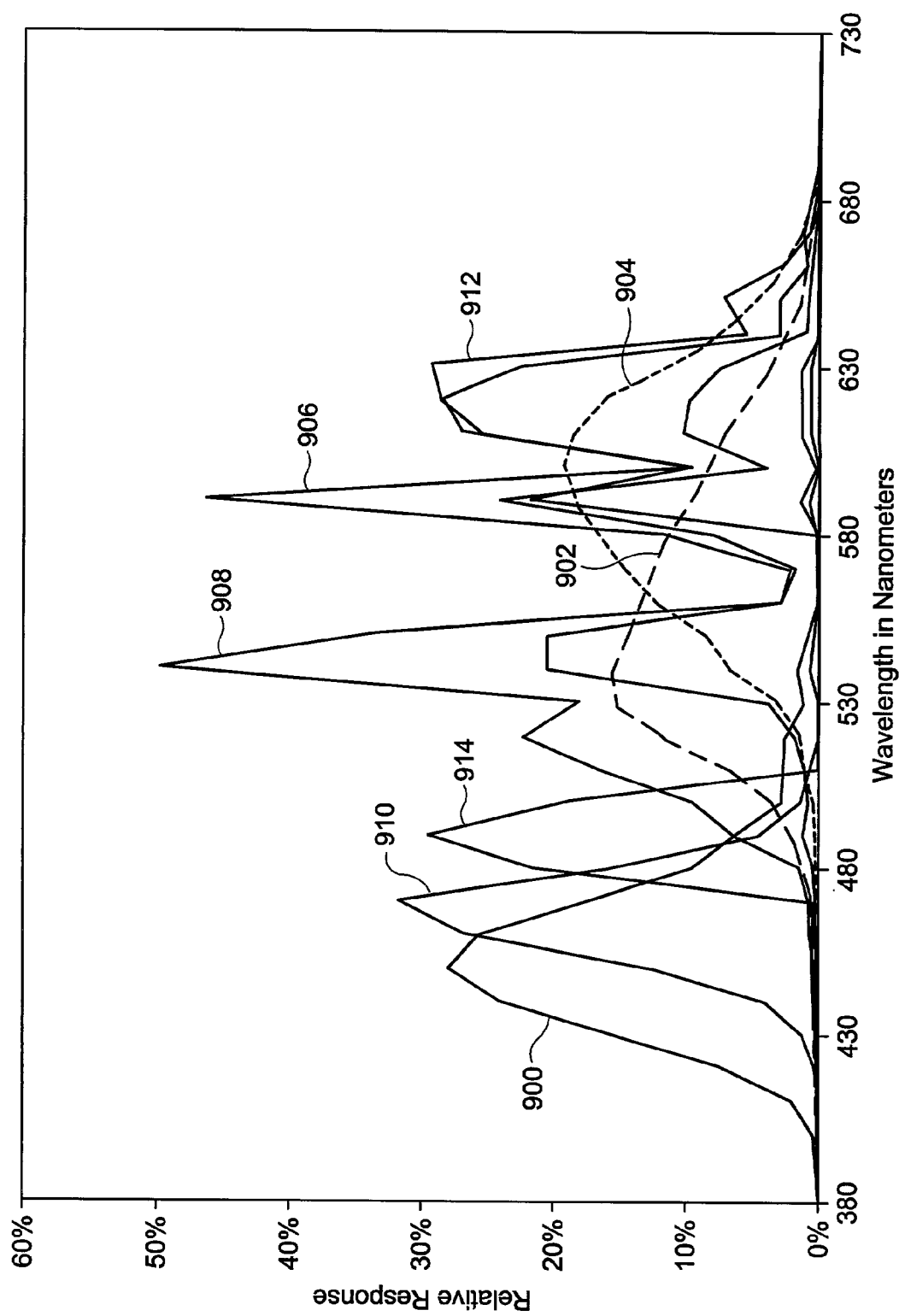

Shown in FIG. 10 are spectral response curves corresponding to the three embodiments of the color measurement device is a simplified drawing showing the layout of the first embodiment of the color measurement device.

DETAILED DESCRIPTION OF THE DRAWINGS

Although embodiments of the color measurement device will be discussed in the context of an inkjet imaging device, such as an inkjet printer, inkjet copying system, inkjet facsimile machine, or the like, it should be recognized that embodiments of the color measurement device could be usefully applied in electrophotographic imaging devices, such as electrophotographic printers, electrophotographic copiers, electrophotographic facsimile machines, or the like.

In addition, embodiments of the color measurement device could be usefully applied for the measurement of colors produced on media by any type imaging device (e.g. a commercial color printing press) capable of forming images on media. Furthermore, embodiments of the color measurement device could be used in a standalone manner to generate color measurements on colored regions formed in arbitrary fashion.

Figure 1:
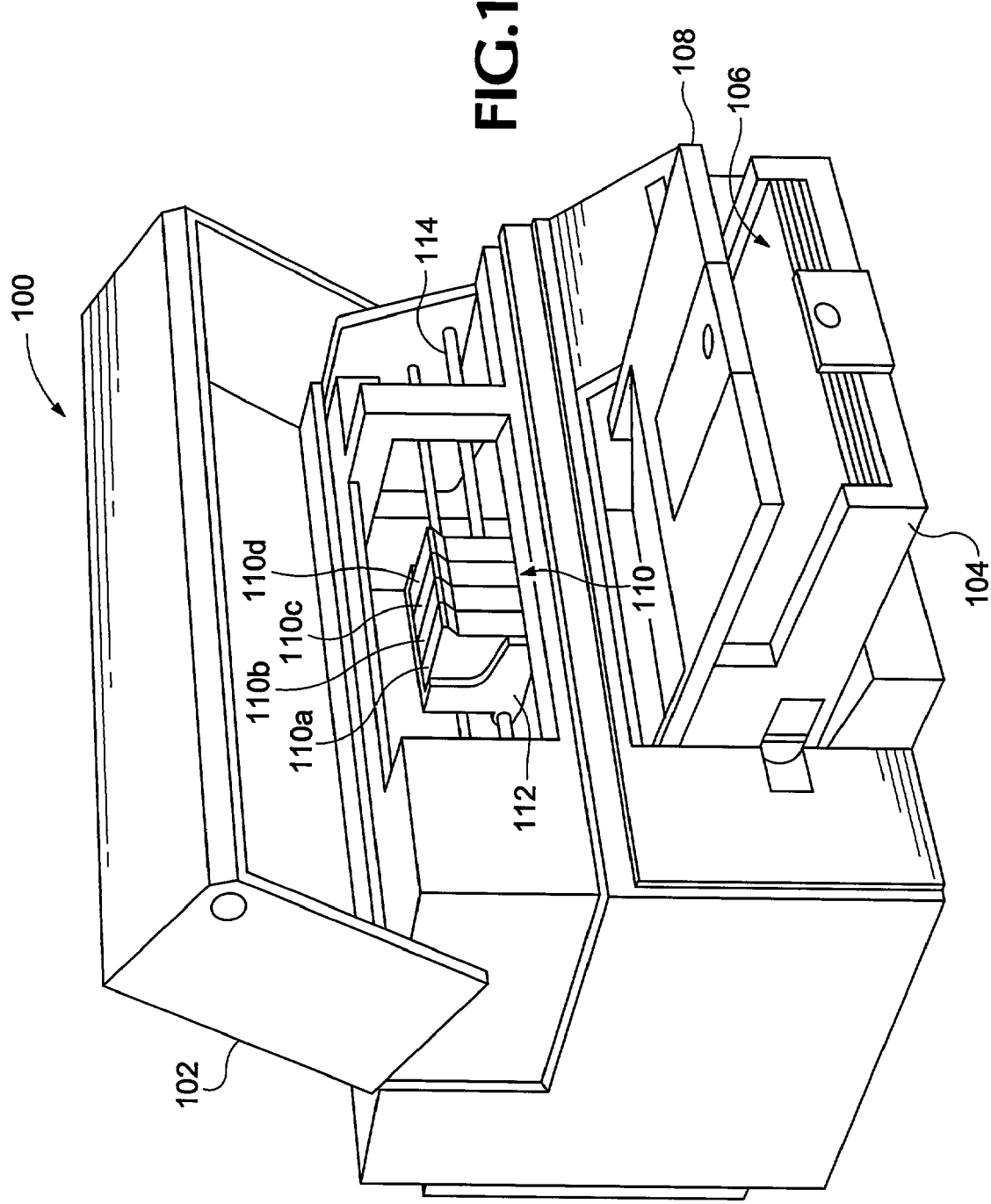

Shown in FIG. 1 is an embodiment of an imaging device, color inkjet printer 100, that includes an embodiment of the color measurement device used in performing an embodiment of the color measurement method. Color inkjet printer 100 includes a cover 102, a media input tray 104 for holding media 106 to be used in an imaging operation, a media output tray 108 for receiving the units of media 106 on which images have been formed, color ink cartridges 110 (including a cyan cartridge 110a, a magenta (M) cartridge 110b, a yellow (Y) cartridge 110c, and a black (K) cartridge 110d), and a scanning carriage 112 for sliding along a slide bar 114 while colorant from one or more of color cartridges 110 is placed onto pixels. In color inkjet printer 100, the colorant stored in color cartridges 110 includes ink.

Shown in FIG. 2 is a block diagram representation of a system used for forming images on media 106 including an embodiment of a color measurement device. The system includes a computer 200. Computer 200 may execute an application program to generate data corresponding to an image displayed on monitor 202 (such as a CRT) or retrieve the data corresponding to the image from a storage device included within computer 200 through the application program. Typically, monitor 202 will display an image using an RGB color space and 24 bits (8 bits for each primary color) to specify the color value for each monitor pixel. An embodiment of an imaging device, printer 204, is coupled to computer 200.

Printer 204 may include color inkjet printer 100 or other types of printers such as an electrophotographic printer. Printer 204 includes the capability to form color images upon media 106 using a set of colorants (such as ink or toner) forming a color space (e.g. cyan, magenta, and yellow and optionally black). Printer 204 may be configured to form images at 300 dpi, 600 dpi, 1200 dpi, or other resolutions. A printer driver program that can execute in computer 200 converts the data (corresponding to the image) received from the application program into a form useable by printer 204, such as a page description language (PDL) file. The PDL file may include for example a file defined in HEWLETT PACKARD'S PCL-3 or PCL-5 format.

Printer 204 renders the PDL file to generate pixel data including a color value for each pixel of each of the color planes forming the image. For example, an embodiment of printer 204 may generate color values for pixels forming the cyan, magenta, yellow, and black color planes. The color values for each of the pixels in the color planes may range, for example, from 0–255. A halftoning operation may be performed upon the color values of the color planes to generate halftone data for the image. The halftone data may include binary or multi-bit data specifying for each of the pixels in each of the color planes whether colorant for that color plane will be placed onto the pixel. Alternatively, the image may be formed using the color values for each of the pixels in each of the color planes without halftoning. For this alternative, the quantity of colorant placed onto the pixel is directly related to the color value for the pixel. For an inkjet printer, the quantity of the colorant is controlled by the number of drops of ink of a specific color placed onto the region of the media corresponding to the pixel. For an electrophotographic printer, the quantity of the colorant is controlled by the fractional portion of the region on the photoconductor corresponding to the pixel that is exposed and developed.

Included in printer 204 is an embodiment of an image forming mechanism, imaging mechanism 206. Imaging mechanism 206 includes the hardware necessary to place colorant on media 106. For example, in the case of an electrophotographic printer, imaging mechanism 206 may include a photoconductor, developing devices for developing cyan, magenta, yellow, and black toner (the colorants in this embodiment of imaging mechanism 206), a photoconductor exposure system for forming a latent electrostatic image on the photoconductor, a charging device for charging the photoconductor, a transfer device for transferring toner from the photoconductor to media 106, and a fixing device for fixing toner to media 106.

An embodiment of a controller, such as controller 208, coupled to imaging mechanism 206 controls the placement of colorant onto media 106 by imaging mechanism 206 making use of the halftone data or color values for the pixels forming each of the color planes. The output from the printer driver software executing in computer 200 is passed through interface 210 to controller 208. Controller 208 includes the capability to render the PDL file received from computer 200 to generate pixel data for each of the pixels forming the image. Controller 208 includes an embodiment of a processing device, such as processor 212 configured to execute firmware or software, or an application specific integrated circuit (ASIC) for controlling the placement of colorant onto media 106 by imaging mechanism 206. In addition, controller 208 includes an embodiment of a memory device, such as memory 214 for storing halftone data or color values for the pixels forming the image.

Printer 204 includes an embodiment of the color measurement device, colorimeter 216. Colorimeter 216 generates values related to XYZ tristimulus color space values from measuring a color calibration image formed onto a unit of media 106 during a color calibration operation. Using these values, processor 212 executes firmware or software to convert the values to XYZ tristimulus color space values. The tristimulus color values are used by processor 212 to adjust the quantities of colorant placed onto media 106 so that the resulting colors more closely correspond to the colors that are intended to result from the color values generated from the PDL file. One way in which the values could be converted to XYZ tristimulus color space values is disclosed in a publication entitled "AN LED BASED SPECTROPHOTOMETRIC INSTRUMENT", published in the journal "COLOR IMAGING: DEVICE-INDEPENDENT COLOR, COLOR HARDCOPY, AND GRAPHIC ARTS IV", proceedings of the SPIE Vol. 3648, pp. 226–236, January, 1999, and incorporated by reference in its entirety into this specification.

Further detail on embodiments of imaging mechanisms used in color electrophotographic imaging devices can be found in U.S. Pat. No. 5,291,251, entitled IMAGE DEVELOPMENT AND TRANSFER APPARATUS WHICH UTILIZED AN INTERMEDIATE TRANSFER FILM, issued to Storlie et. al., and assigned to Hewlett-Packard Company, and U.S. Pat. No. 5,314,774, entitled METHOD AND APPARATUS FOR DEVELOPING COLOR IMAGES USING DRY TONERS AND AN INTERMEDIATE TRANSFER MEMBER, issued to Camis, and assigned to Hewlett-Packard Company. Each of these two patents is incorporated by reference in their entirety into this specification.

In the case of a color inkjet printer, imaging mechanism 206 may include ink cartridges movably mounted on a carriage with its position precisely controlled by a belt driven by a stepper motor. An ink cartridge driver circuit coupled to the controller and the ink cartridges fires nozzles in the ink cartridges based upon signals received from the controller to place colorant on media 106 according to the halftone data or color values for the pixels forming each of the color planes. Further detail on embodiments of imaging mechanisms used in color inkjet printers can be found in U.S. Pat. No. 6,082,854, entitled MODULAR INK-JET HARD COPY APPARATUS AND METHODOLOGY, issued to Axtell et al., and assigned to Hewlett-Packard Company, and U.S. Pat. No. 5,399,039, entitled INK-JET PRINTER WITH PRECISE PRINT ZONE MEDIA CONTROL, issued to Giles et al., and assigned to Hewlett-Packard Company. Each of these two patents is incorporated by reference in their entirety into this specification.

Shown in FIG. 3 is a high level flow diagram of a method for forming an image on media using the system of FIG. 2. First, in step 300, a user creates data (or retrieves data) corresponding to an image on monitor 202 using the application program executing in computer 200. Next, in step 302, the user initiates execution of the printer driver program residing in computer 200 through the application program to begin the imaging operation. Then, in step 304, the driver program converts the data into a PDL file including image data useable by printer 204. The image data corresponds to the image on monitor 202 and is expressed in the RGB color space. Next, in step 306, the PDL file is rendered to generate pixel data for each pixel for the R, G, and B color planes. It should be recognized that the rendering operation may be performed in computer 200 or in printer 204. Then, in step 308, a color space conversion is performed to convert the color values for each pixel in the R, G, and B color planes into color values for each pixel in the C, M, Y, and K planes.

It should be recognized that although the method for forming an image is discussed in the context of printer 204 making use of cyan, magenta, yellow, and black colorants to form images, embodiments of the color measurement device could be usefully applied in imaging devices that use other types of colorants to form images. For example, embodiments of the color measurement device could be used in inkjet imaging devices that make use of low dye load cyan colorant and low dye load magenta colorant. Or, embodiments of the color measurement device could be used in imaging devices that make use of orange colorant and green colorant in addition to other colorants. Next, in step 310, an embodiment of a halftoning method is applied to the color values for the pixels in the C, M, Y, and K planes forming the image to generate halftone data. The halftone data indicates for every pixel in the image, in a binary fashion, whether each of the cyan, magenta, yellow, or black colorants are to be applied to the pixel. It should be recognized that the embodiment of the halftoning method could be performed within computer 200 or within controller 208. Finally, in step 312, the image is formed on media 106 by printer 204 using the halftone data. Instead of performing the embodiment of the halftone method in step 310, step 312 could involve formation of the image on media 106 by directly placing colorant onto pixels forming the image according to the color values associated with each pixel.

Shown in FIG. 4 is a simplified block diagram of a first embodiment of the color measurement device, calorimeter 400. Colorimeter 400 includes first source 402. Colorimeter 400 further includes second source 404 and third source 406. Colorimeter 400 also includes first detector 408, second detector 410 and third detector 412. First detector 408, second detector 410, and third detector 412 each generate an electrical output corresponding to the intensity of the light impinging upon the detection elements included within them. Each of these detectors effectively perform an integration, according to their spectral response over the range visible light frequencies, of the light that impinges upon them. Each of first detector 408, second detector 410, and third detector 412 have associated with them, respectively, first filter 414, second filter 416, and third filter 418. These filters are attached to the detectors so that the light impinging upon each of the detectors is first filtered by its corresponding filter. The outputs generated by each of the three detectors include an analog signal, such as an analog current or analog voltage, corresponding to the integrated spectrum of the light impinging upon each of the detectors (having a spectrum modified by the corresponding filter). The outputs are coupled to an embodiment of a conversion device, such as conversion device 420. Conversion device 420 could include an analog to digital converter to generate three corresponding digital values from the analog signals. The analog to digital converter could include three channels and three outputs having the capability to convert the analog signals contemporaneously or the analog to digital converter could include a multiplexer to perform the conversion from the analog signals to the corresponding digital values sequentially.

The light that impinges upon each of first detector 408, second detector 410, and third detector 412 is formed from diffuse reflection off the surface of color test print 422. Color test print 422 includes a unit of media 106 onto which multiple horizontal bars of colored regions are formed, of which colored region 424 is exemplary. Some of the colors of the colored regions used include for example cyan, magenta, yellow, green, red, and blue. Colorimeter 400 is physically configured so that the groups of sources and detector filter combinations are arranged in a line orientated substantially perpendicular to the direction the unit of media 106 moves. By forming the colored regions into bars across the width of media 106, the groups of sources, filters, and detectors can gather sets of measurement on multiple colored regions having substantially the same hue and chroma while remaining stationary and moving a unit of media 106 having the colored regions past calorimeter 400. This configuration of colorimeter 400 is well adapted for placement adjacent to a media path in an imaging device to make measurements upon units of media. It should be recognized, however, that embodiments of a color measuring device could be configured so that they are movable with respect to units of media. In addition, embodiments of the color measuring device could be configured so that the sources and detectors can be individually moved into position for making measurements upon units of media. Additional information on the configuration of embodiments of the color measuring device can be found in copending U.S. patent application Ser. No. 09/768,662, entitled "COLOR MEASUREMENT WITH DISTRIBUTED SENSORS IN A COLOR HARD COPY APPARATUS", assigned to Hewlett-Packard Company, and incorporated by reference in its entirety into this specification.

Colorimeter 400 includes three sets of corresponding sources, filters, and detectors. For each of these three sets, a spectral response is formed by the combination of the light source, the filter, and the detector. The spectral response can be determined as the product of the individual spectral responses of the three components. That is, the product of the emission spectrum of the light source, the spectral response of the filter, and the spectral response of the detector. By selecting the spectral response of one or more of the light source, the filter, or the detector, a desired overall spectral transfer function can be established. Ideally, the overall spectral transfer functions of each of the groups of three components would closely approximate, if not exactly match, the color matching functions used in computation of the XYZ tristimulus values. It should be recognized that although embodiments of the color measuring device will be discussed in the context of generating values used in the computation of XYZ tristimulus values, embodiments of the color measuring device could be used to determine values for other tristimulus color specification systems.

Shown in FIG. 5 are graphs showing the color matching functions each corresponding to one of the components of the XYZ tristimulus values. Curve 500 corresponds to the color matching function for the X component. Curve 502 corresponds to the color matching function for the Y component. Curve 504 corresponds to the color matching function for the Z component. By properly selecting the sources, filters, and detectors, calorimeter 400 has spectral transfer functions that are sufficiently close in shape to the XYZ color matching functions so that further mathematical transformation applied to these values will convert them to a close approximation of the tristimulus values, useful for determining the perceived color of the region measured.

As previously mentioned, use of a set of sources, filters, and detectors can produce spectral transfer functions that can sufficiently approximate the XYZ color matching functions so that the resulting values are useful for computing the XYZ tristimulus values. One set of sources that can be used to form the desired spectral transfer functions makes use of a so called "white light" LED for first source 402 and second source 404. In addition, a xenon bulb is used for third source 406. Shown in FIG. 6A are typical spectral emission curves for the case in which first source 402 and second source 404 are white light LEDs. Curve 510 represents the typical spectral emission curve for a white light LED. Curve 512 represents the spectral emission curve for a particular xenon bulb. Curve 514 represents the spectral emission curve for a particular blue LED. This xenon bulb generates its emission spectrum using a combination of the light emitted by the gas discharge and the light emitted from the fluorescing phosphors included within it. As can be seen from curve 512, there is substantial non-uniformity in the magnitude of the spectral response from the xenon bulb and the white light LED. It should be emphasized that although curve 510 and curve 512 represent the spectral response of, respectively, a particular type of white LED and a particular type of xenon bulb, other types of solid state lamps and gas discharge tubes could be usefully applied in colorimeter 400. For example, a solid state lamp making use of an incandescent filament and having the appropriate emission spectrum could be used. Or, a solid state lamp that uses electroluminescent materials (an electroluminescent lamp) and having the appropriate emission spectrum could be used. Or, a gas discharge tube that generates its emission spectrum primarily using fluorescing phosphors (such as a type of fluorescent lamp used in a scanner) and has the appropriate emission spectrum could be used. Or, a gas discharge tube that generates its emission spectrum primarily using gas discharge and has the appropriate emission spectrum could be used. Furthermore, other types of light sources having spectral emission characteristics that are similar to those of curve 500 and curve 502 could be usefully applied in calorimeter 400. A type of white light LED that substantially corresponds to curve 500 is sold by Nichia American Corporation. This type of white light LED uses a blue semiconductor light emitting diode and a phosphor that absorbs the blue light and emits a yellow light to generate the spectral emission characteristic substantially corresponding to curve 510. A type of xenon bulb that substantially corresponds to curve 512 is sold by NEC and has part number CFX8AEXD/17BB.

Shown in FIG. 7 is a more detailed representation of the physical arrangement of one of the LED, filter, and detector combinations. Light emitted from LED 600, included within source 601, is directed onto a region on the plane of color test print 422 using lens 602. LED 600 and lens 602 are orientated so that a portion of one of the colored regions on color test print 422 will be illuminated. The distance from lens 602 and the surface of color test print 422 is selected with the objective of maximizing the illumination of the region on the surface of color test print 422 from which light is collected by detector 605. Optimally, the region on the surface of color test print 422 from which light is collected by detector 605 would have illumination of substantially uniform intensity throughout the region with no illumination outside of the region. However, it should be recognized that embodiments of calorimeter 400 using less than optimal illumination perform adequately. Techniques to illuminate the region in the desired manner are disclosed in U.S. Pat. No. 6,036, 298, entitled "MONOCHROMATIC OPTICAL SENSING SYSTEM FOR INKJET PRINTING", assigned to Hewlett Packard Company, and incorporated by reference in its entirety into this specification. Lens 604, included within detector 605 gathers the diffuse reflected light from the colored region on the surface of color test print 422. Lens 604 is positioned to direct the light it gathers onto the surface of optical sensor 606. The diffuse reflected light gathered by lens 604 passes through filter element 608 and aperture stop 609 before impinging upon the surface of optical sensor 606 so that the filter function is applied to the collected light. Aperture stop 609 eliminates the diffuse reflected light from the edges of the illuminated region and beyond so that the diffuse reflected light impinging upon optical sensor 606 primarily comes from portions of the region having a substantially uniform illumination. LED 600 and optical sensor 606 are located with respect to each other so that the light impinging upon optical sensor 606 includes primarily the diffuse reflected light from the colored regions on color test print 422, with only a relatively minor contribution from the specular reflection. One angle that could be used between orientation of LED 600 and optical sensor 606 is 45 degrees. It should be recognized that useful embodiments of calorimeter 400 could be constructed that do not use a lens for directing the light from the LEDs or for collecting the diffuse reflected light and directing it onto the detectors. In calorimeter 400, a lens is not used for directing the light emitted by the xenon bulb onto color test print 422. But, the xenon bulb is orientated with respect to its corresponding detector so that there is approximately 45 degrees between them.

First filter 414, second filter 416, and third filter 418 are designed taking into consideration the spectral emission characteristics of the corresponding source that each is filtering, the spectral response of the detectors over the range of wavelengths impinging upon the detectors, and the XYZ tristimulus color matching function that it is desired to match. For the detectors selected for calorimeter 400, the magnitude of the spectral response (as a function of the light energy incident upon the detector) is constantly increasing over the range of the wavelengths of interest. Shown in FIG. 6B is typical spectral response curve for a detector that could be used within calorimeter 400 showing the constantly increasing response magnitude with increasing wavelength. As previously mentioned the overall spectral response of the source-filter-detector system is determined as the product of the spectral response curves of each of the components. Therefore, the desired filter spectral response is determined by dividing the corresponding color matching function (for either the X, Y, or Z component of the tristimulus value) by the product of the spectral emission characteristic of the corresponding source and the spectral response of the detector. The resulting desired filter spectral response is used as the basis to design the corresponding one of first filter 414, second filter 416, and third filter 418. One type of optical filter technology that could be used for implementing first filter 414, second filter 416, and third filter 418 is a thin film interference filter. A thin film interference filter includes a multiplicity of layers formed of a material and thickness so that each layer provides a portion of the desired spectral response curve for the filter. Together, the layers provide a spectral response that approximates the desired filter spectral response. First filter 414 is designed so that its output will contribute to approximating the tristimulus color matching function corresponding to the X component. Second filter 416 is designed so that its output will contribute to approximating the tristimulus color matching function corresponding to the Y component. Third filter 418 is designed so that its output will contribute to approximating the tristimulus color matching function corresponding to the Z component. Thin film interference filters that will provide an acceptable spectral response for colorimeter 400 can be fabricated by Optical Coating Laboratory Incorporated of Santa Rosa, Calif. if they are provided with the desired spectral response curve for the filter. It should be recognized that although embodiments of the color measurement device make use of a thin film interference, other types of optical filters could be used to provide the desired spectral response.

Colorimeter 400 can be used in several ways to gather measurement data useful for determining XYZ tristimulus values for a colored region. A first way includes illuminating the LEDs in first source 402 and second source 404 (either substantially contemporaneously or sequentially) to obtain measured values from first detector 408 and second detector 410 used for determining, respectively, the X component and the Y component. The xenon bulb included in third source 406 is illuminated either before or after the illumination of first source 402 and second source 404 to obtain a measured value for determining the Z component from third detector 412. Furthermore, third source 406 could be illuminated substantially contemporaneously with either or both of first source 402 and second source 404. In this mode of operation, the effects of third source 406 upon the output from first detector 408 and second detector 410 are determined by illuminating third source 406 only and measuring the output from first detector 408 and second detector 410. Then, the measured contribution of the diffuse reflected light from third source 406 to the outputs from first detector 408 and second detector 410, while first source 402 and second source 404 are illuminated, is subtracted from the outputs of first detector 408 and second detector 410. The order of illumination of the sources is arbitrary. In using colorimeter 400 this first way, three measured values are obtained that are used to determine the XYZ tristimulus values for the colored region. The three measured values are the result of an optical integration of the spectral response function formed from the product of the source spectral emission characteristic, the spectral response caused by the diffuse reflection from the colored region, the filter spectral response, and the detector spectral response using colorimeter 400. A second way in which colorimeter 400 may be used includes performing all of the measurements specified in the first way and in addition two other measurements. The two additional measurements include illuminating the xenon bulb in third source 406 and measuring the output from first detector 408 and second detector 410. The measurement of the output could be done substantially contemporaneously or in sequence by successively illuminating third source 406, once for first detector 408 and second detector 410. The additional two measurements provide two values that are combined, through a mathematical transformation, with the three values previously measured to more closely approximate the XYZ tristimulus values. The additional two measurements (from first detector 408 measuring diffuse reflected light from third source 406 and from second detector 410 measuring diffuse reflected light third source 406) are used to improve the accuracy of the approximation of the X component, the Y component, and the Z component of the XYZ tristimulus value. The additional two measurements provide useful information to improve the accuracy of the approximation of each of the components of the XYZ tristimulus value because the emission spectrum of third source 406 includes energy at wavelengths included in the X color matching function, the Y color matching function, and the Z color matching function. One way in which to perform the mathematical transformation for combining the two additional measurements involves matrix manipulations. Conceptually, the addition of these two values can be regarded as modifying the system spectral response so that the result of the optical integration more closely correspond to what would result if the exact XYZ tristimulus color matching functions were used to measure the diffuse reflected light from colored regions on color test print 422. Using colorimeter 400 in the second way provides a more accurate estimation of the XYZ tristimulus values without the addition of more hardware.

Shown in FIG. 8 is a simplified block diagram of a second embodiment of a color measurement device, calorimeter 700. The second embodiment of the color measurement device is formed by adding fourth source 702 to calorimeter 400. Fourth source 702 may include a blue light LED, such as one of the blue light LEDs supplied by Agilent Technology Corporation. The fourth source 702 is physically located so that third detector 412 views the diffuse reflected light from color test print 422 resulting from the illumination of fourth source 702 substantially at a 45 degree angle. Measurement of the diffuse reflected light resulting from the illumination of fourth source 702 may be done when the xenon bulb of third source 406 is not illuminated or, using the previously described technique of removing the effect of third source 406 on the output of third detector 412, measurement may be done when the xenon bulb of third source 406 is illuminated. The value measured from third detector 412 resulting from the illumination of fourth source 702 is combined, through a mathematical transformation, with the values previously measured for the X component, the Y component, and the Z component of the XYZ tristimulus value. Combining these values provides a more accurate estimation of the components of the XYZ tristimulus value. The measurement of the diffuse reflected light from fourth source 702 using third detector 412 provides additional information about the spectral characteristics of the diffuse reflection enabling more accurate estimates of the X, Y, and Z components.

Shown in FIG. 9 is a simplified block diagram of a third embodiment of a color measurement device, calorimeter 800. The third embodiment of the color measurement device is formed by adding two additional detectors to colorimeter 700. Fourth detector 802 includes fourth filter 804 having a bandpass spectral response characteristic centered around the 490 nanometer wavelength. Fifth detector 806 includes a fifth filter 808 having a bandpass spectral response characteristic centered around the 627 nanometer wavelength. One way in which the center wavelengths of fourth filter 804 and fifth filter 808 can be selected involves iterative numerical simulations of the system spectral response in which bandpass spectral responses of filters having different center wavelengths are used to generate simulated values. These simulated values are combined, through a mathematical transformation, with values derived from a simulation of the system spectral response of the other components to form simulated X component, Y component, and Z component tristimulus values. The simulated XYZ tristimulus values are compared to the ideal XYZ tristimulus values. Then, the center wavelengths of the filters are adjusted according to this comparison so that the simulated X component, Y component, and Z component tristimulus values more accurately estimate the ideal XYZ tristimulus values. It should be recognized that as the spectral response of one or more of the system components changes (detectors, sources, or filters) the center wavelengths of the bandpass filters that are selected will also change. Furthermore, the simulation may be performed without consideration of noise (i.e. random variations in the detector outputs that can result from random processes operating in any of the system components) in the measurements. Consideration of the noise in the system can also shift the selected center wavelengths of the bandpass filters or potentially show that better results may be achieved without using the additional bandpass filters.

The xenon bulb included in third source 406 is illuminated and values are measured from fourth detector 802 and fifth detector 806 either substantially contemporaneously or sequentially. The value obtained from fourth detector 802 is combined with the X component, Y component, and Z component measurements (the same ones that would be obtained through operating colorimeter 700) to improve the accuracy of the XYZ tristimulus value. The value obtained from fifth detector 806 is combined with the X component, Y component, and Z component measurements (the same ones that would be obtained through operating colorimeter 700) to further improve the accuracy of the XYZ tristimulus value. It should be recognized that although fourth filter 804 and fifth filter 808 are configured to have a bandpass response around specific frequencies, other shapes and center frequencies of filters could be selected. For example if the spectral emission response of third source 406 were different from that of the typical xenon bulb, a filter having a different shape or center frequency may be used to yield the desired results. Conversion device 810 includes 5 channels to measure the outputs of the five detectors.

Shown in FIG. 10 are a set of spectral response curves for the eight aggregated transfer functions formed from the combinations of illumination source, filter, detector discussed for the first, second, and third embodiments of the color measurement device. Curve 900 is the spectral response resulting from the combination of third source 406, third filter 418, and third detector 412 used to approximate the Z color matching function. Curve 902 is the spectral response resulting from the combination of second source 404, second filter 416, and second detector 410 used to approximate the Y color matching function. Curve 904 is the spectral response resulting from the combination of first source 402, first filter 414, and first detector 408 used to approximate the X color matching function. Curve 906 is the spectral response resulting from the combination of third source 406, first filter 414, and first detector 408. Curve 908 is the spectral response resulting from the combination of third source 406, second filter 416, and second detector 410. Curve 910 is the spectral response resulting from the combination of fourth source 702, third filter 418, and third detector 412. Curve 912 is the spectral response resulting from the combination of third source 406, fourth filter 804, and fourth detector 802. Curve 914 is the spectral response resulting from the combination of third source 406, fifth filter 808, and fifth detector 806.

Although embodiments of the color measurement device have been illustrated, and described, it is readily apparent to those of ordinary skill in the art that various modifications may be made to these embodiments without departing from the scope of the appended claims.

What is claimed is:

1. A method, comprising:
   illuminating a first portion of a colored region with first light from a gas discharge tube;
   generating a first output using a diffuse reflection of the first light from the first portion;
   illuminating a second portion of the colored region with second light from a first solid state lamp;
   generating a second output using a diffuse reflection of the second light from the second portion;
   illuminating a third portion of the colored region with third light from a second solid state lamp; and
   generating a third output using a diffuse reflection of the third light from the third portion.

2. The method as recited in claim 1, wherein:
   with the first light having a first spectrum, generating the first output includes filtering the diffuse reflection of the first light according to a first filter spectral response to generate a first filtered diffuse reflection of the first light and measuring an intensity of the first filtered diffuse reflection to form the first output;
   with the second light having a second spectrum, generating the second output includes filtering the diffuse reflection of the second light according to a second filter spectral response to generate a second filtered diffuse reflection of the second light and measuring an intensity of the second filtered diffuse reflection to form the second output; and
   with the third light having a third spectrum, generating the third output includes filtering the diffuse reflection of the third light according to a third filter spectral response to generate a third filtered diffuse reflection of the third light and measuring an intensity of the third filtered diffuse reflection to form the third output.

3. The method as recited in claim 2, wherein:
   the first filter spectral response approximates a first spectral response formed using a ratio of a Z tristimulus color matching function to a product of a first detector spectral response and the first spectrum, where the first detector generates the first output;
   the second filter spectral response approximates a second spectral response formed using a ratio of a X tristimulus color matching function to a product of a second detector spectral response and the second spectrum, where the second detector generates the second output; and
   the third filter spectral response approximates a third spectral response formed using a ratio of a Y tristimulus color matching function to a product of a third detector spectral response and the third spectrum, where the third detector generates the third output.

4. The method as recited in claim 3, wherein:
the first gas discharge tube includes a xenon lamp;
the first solid state lamp includes a first white light LED;
the second solid state lamp includes a second white light LED; and
the first portion includes the second portion and the third portion.

5. The method as recited in claim 3, further comprising:
generating a fourth output using a fourth filtered diffuse reflection of the first light from the first portion by filtering the diffuse reflection of the first light according to the second filter spectral response to generate the fourth filtered diffuse reflection of the first light and measuring an intensity of the fourth filtered diffuse reflection to form the fourth output; and
generating a fifth output using a fifth filtered diffuse reflection of the first light from the first portion by filtering the diffuse reflection of the first light according to the third filter spectral response to generate the fifth filtered diffuse reflection of the first light and measuring an intensity of the fifth filtered diffuse reflection to form the fifth output.

6. The method as recited in claim 5, wherein:
the first gas discharge tube includes a xenon lamp;
the first solid state lamp includes a first white light LED; and
the second solid state lamp includes a second white light LED.

7. The method as recited in claim 5, further comprising:
illuminating a fourth portion of the colored region with fourth light from a third solid state lamp; and
generating a sixth output using a sixth filtered diffuse reflection of the fourth light from the fourth portion by filtering the diffuse reflection of the fourth light according to the first filter spectral response to generate the sixth filtered diffuse reflection of the fourth light and measuring an intensity of the sixth filtered diffuse reflection to form the sixth output.

8. The method as recited in claim 7, wherein:
the third solid state lamp includes a blue light LED.

9. The method as recited in claim 7, further comprising:
generating a seventh output using a seventh filtered diffuse reflection of the first light from the first portion by filtering the diffuse reflection of the first light according to a fourth filter spectral response to generate the seventh filtered diffuse reflection of the first light and measuring an intensity of the seventh filtered diffuse reflection to form the seventh output; and
generating an eighth output using an eighth filtered diffuse reflection of the first light from the first portion by filtering the diffuse reflection of the first light according to a fifth filter spectral response to generate the eighth filtered diffuse reflection of the first light and measuring an intensity of the eighth filtered diffuse reflection to form the eighth output.

10. The method as recited in claim 9, wherein:
the fourth filter spectral response corresponds to that of a first bandpass filter having a center wavelength substantially equal to 627 nanometers;
the fifth filter spectral response corresponds to that of a second bandpass filter having a center wavelength substantially equal to 490 nanometers; and
the first portion includes the second portion, the third portion, and the fourth portion.

11. A color measurement device comprising:
a gas discharge tube to illuminate a first portion of a colored region with first light having a first spectrum;
a first detector having a first detector spectral response and positioned to receive a first filtered diffuse reflection of the first light to generate a first output;
a first filter having a first spectral response formed using a ratio of a Z tristimulus color matching function to a product of the first detector spectral response and the first spectrum and positioned to receive a first diffuse reflection of the first light to generate the first filtered diffuse reflection;
a first solid state lamp to illuminate a second portion of the colored region with second light having a second spectrum;
a second detector having a second detector spectral response and positioned to receive a second filtered diffuse reflection of the second light to generate a second output;
a second filter having a second spectral response formed using a ratio of a X tristimulus color matching function to a product of the second detector spectral response and the second spectrum and positioned to receive a second diffuse reflection of the second light to generate the second filtered diffuse reflection;
a second solid state lamp to illuminate a third portion of the colored region with third light having a third spectrum;
a third detector having a third detector spectral response and positioned to receive a third filtered diffuse reflection of the third light to generate a third output; and
a third filter having a third spectral response formed using a ratio of a Y tristimulus color matching function to a product of the third detector spectral response and the third spectrum and positioned to receive a third diffuse reflection of the third light to generate the third filtered diffuse reflection.

12. The color measurement device as recited in claim 11 wherein:
the first gas discharge tube includes a xenon lamp;
the first solid state lamp includes a first white light LED;
the second solid state lamp includes a second white light LED; and
the first portion includes the second portion and the third portion.

13. The color measurement device as recited in claim 11, wherein:
the second detector includes a position to receive a fourth filtered diffuse reflection of the first light to generate a fourth output;
the second filter includes a position to receive the first diffuse reflection of the first light to generate the fourth filtered diffuse reflection;
the third detector includes a position to receive a fifth filtered diffuse reflection of the first light to generate a fifth output; and
the third filter includes a position to receive the first diffuse reflection of the first light to generate the fifth filtered diffuse reflection.

14. The color measurement device as recited in claim 13, further comprising:
a third solid state lamp to illuminate a fourth portion o f the colored region with fourth light having a fourth spectrum, where the first detector includes a position to receive a sixth filtered diffuse reflection of the fourth light to generate a sixth output and the first filter includes a position to receive a diffuse reflection of the fourth light to generate the sixth filtered diffuse reflection.

15. The color measurement device as recited in claim 14, wherein:
the third solid state lamp includes a blue light LED.

16. The color measurement device as recited in claim 14, further comprising:
a fourth detector positioned to receive a seventh filtered diffuse reflection of the first light to generate a seventh output;
a fourth filter including a fourth spectral response having a first bandpass shape and positioned to receive the first diffuse reflection of the first light to generate the seventh filtered diffuse reflection;
a fifth detector positioned to receive an eighth filtered diffuse reflection of the first light to generate an eighth output; and
a fifth filter including a fifth spectral response having a second bandpass shape and positioned to receive the first diffuse reflection of the first light to generate the eighth filtered diffuse reflection.

17. The color measurement device as recited in claim 16, wherein:
the first bandpass shape includes a center wavelength of 627 nanometers;
the second bandpass shape includes a center wavelength of 490 nanometers; and
the first portion includes the second portion, the third portion, and the fourth portion.

18. A calorimeter, comprising:
a xenon tube to illuminate a first portion of a colored region with first light having a first spectrum;
a first detector positioned to receive a first filtered diffuse reflection of the first light to generate a first output and having a first detector spectral response;
a first filter having a first spectral response formed using a ratio of a Z tristimulus color matching function to a product of the first detector spectral response and the first spectrum and positioned to receive a first diffuse reflection of the first light to generate the first filtered diffuse reflection;
a first white light LED to illuminate a second portion of the colored region with second light having a second spectrum;
a second detector positioned to receive a second filtered diffuse reflection of the second light to generate a second output and having a second detector spectral response;
a second filter having a second spectral response formed using a ratio of a X tristimulus color matching function to a product of the second detector spectral response and the second spectrum and positioned to receive a second diffuse reflection of the second light to generate the second filtered diffuse reflection;
a second white light LED to illuminate a third portion of the colored region with third light having a third spectrum;
a third detector positioned to receive a third filtered diffuse reflection of the third light to generate a third output and having a third detector spectral response; and
a third filter having a third spectral response formed using a ratio of a Y tristimulus color matching function to a product of the third detector spectral response and the third spectrum and positioned to receive a third diffuse reflection of the third light to generate the third filtered diffuse reflection.

19. An imaging device, comprising:
an interface arranged to receive data from a computer;
an image forming mechanism configured to form an image on media corresponding to image data;
a color measurement device including a gas discharge tube to illuminate a first portion of a colored region on the media with first light having a first spectrum, a first detector having a first detector spectral response and positioned to receive a first filtered diffuse reflection of the first light to generate a first output, a first filter having a first spectral response formed using a ratio of a Z tristimulus color matching function to a product of the first detector spectral response and the first spectrum and positioned to receive a first diffuse reflection of the first light to generate the first filtered diffuse reflection, a first solid state lamp to illuminate a second portion of the colored region with second light having a second spectrum, a second detector having a second detector spectral response and positioned to receive a second filtered diffuse reflection of the second light to generate a second output, a second filter having a second spectral response formed using a ratio of a X tristimulus color matching function to a product of the second detector spectral response and the second spectrum and positioned to receive a second diffuse reflection of the second light to generate the second filtered diffuse reflection, a second solid state lamp to illuminate a third portion of the colored region with third light having a third spectrum, a third detector having a third detector spectral response and positioned to receive a third filtered diffuse reflection of the third light to generate a third output, and a third filter having a third spectral response formed using a ratio of a Y tristimulus color matching function to a product of the third detector spectral response and the third spectrum and positioned to receive a third diffuse reflection of the third light to generate the third filtered diffuse reflection;
a processing device configured to determine XYZ tristimulus values using the first output, the second output, and the third output received from the color measurement device and configured to generate the image data using the data received from the interface; and
a memory to store the data and the image data.

20. A color measurement device comprising:
means for illuminating a first portion of a colored region with first light having a first spectrum corresponding to a xenon bulb;
first means for detecting having a first detecting spectral response and positioned to receive a first filtered diffuse reflection of the first light to generate a first output;
first means for filtering having a first spectral response formed using a ratio of a Z tristimulus color matching function to a product of the first detecting spectral response and the first spectrum and positioned to receive a first diffuse reflection of the first light to generate the first filtered diffuse reflection;
means for illuminating a second portion of the colored region with second light having a second spectrum corresponding to a white light LED;

second means for detecting having a second detecting spectral response and positioned to receive a second filtered diffuse reflection of the second light to generate a second output;

second means for filtering having a second spectral response formed using a ratio of a X tristimulus color matching function to a product of the second detecting spectral response and the second spectrum and positioned to receive a second diffuse reflection of the second light to generate the second filtered diffuse reflection;

means for illuminating a third portion of the colored region with third light having a third spectrum corresponding to a white light LED;

third means for detecting having a third detecting spectral response and positioned to receive a third filtered diffuse reflection of the third light to generate a third output; and third means for filtering having a third spectral response formed using a ratio of a Y tristimulus color matching function to a product of the third detecting spectral response and the third spectrum and positioned to receive a third diffuse reflection of the third light to generate the third filtered diffuse reflection.

* * * * *